United States Patent [19]
Källström et al.

[11] Patent Number: 5,900,424
[45] Date of Patent: May 4, 1999

[54] OMEPRAZOLE MAGNESIUM SALT FORM

[75] Inventors: Lars Åke Källström; Monica Annelie Nygren, both of Södertälje, Sweden

[73] Assignee: Astra Aktiebolag, Sodertalje, Sweden

[21] Appl. No.: 08/313,342

[22] PCT Filed: Jul. 8, 1994

[86] PCT No.: PCT/SE94/00680

§ 371 Date: Sep. 27, 1994

§ 102(e) Date: Sep. 27, 1994

[87] PCT Pub. No.: WO95/01977

PCT Pub. Date: Jan. 19, 1995

[30] Foreign Application Priority Data

Jul. 9, 1993 [SE] Sweden .................................. 9302396

[51] Int. Cl.$^6$ ......................... C07D 401/12; A61K 31/44
[52] U.S. Cl. ........................................ 514/338; 546/273.7
[58] Field of Search .......................... 546/273.7; 514/338

[56] References Cited

FOREIGN PATENT DOCUMENTS

| 0005129 | 4/1981 | European Pat. Off. . |
|---|---|---|
| 0124495 | 1/1987 | European Pat. Off. . |
| 4035455 | 11/1990 | Germany . |
| 9501977 | 7/1994 | WIPO . |

OTHER PUBLICATIONS

Drug Development and Industrial Pharmacy, 19(6), 631–641, Labhasetwar et al., 1993.

Kohl et al. CA 117:90285, 1992.

Primary Examiner—Jane Fan
Attorney, Agent, or Firm—White & Case L.L.P.

[57] ABSTRACT

A novel compound form of magnesium omeprazole useful in the manufacture of pharmaceutical formulations, the use of the product and the process for its production are described.

22 Claims, 1 Drawing Sheet

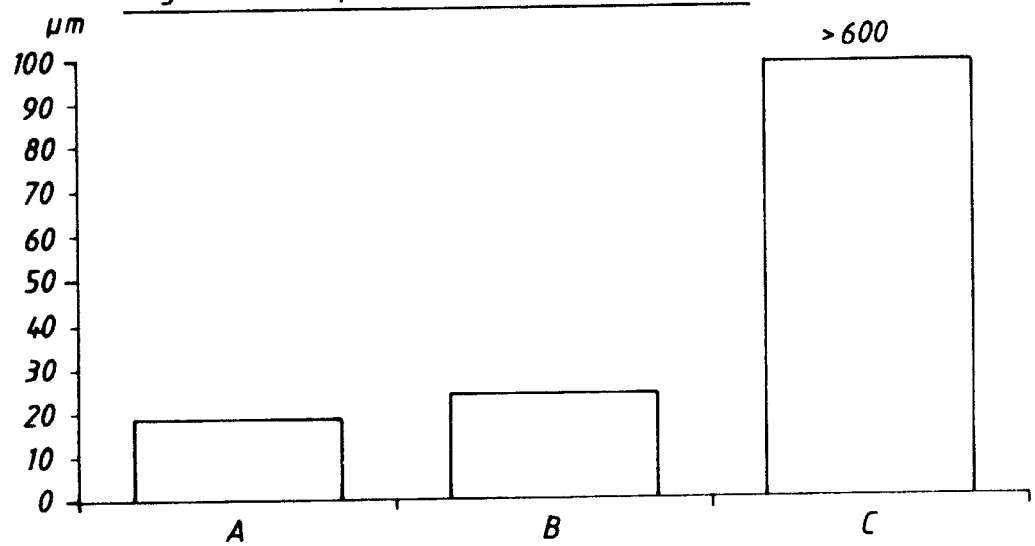
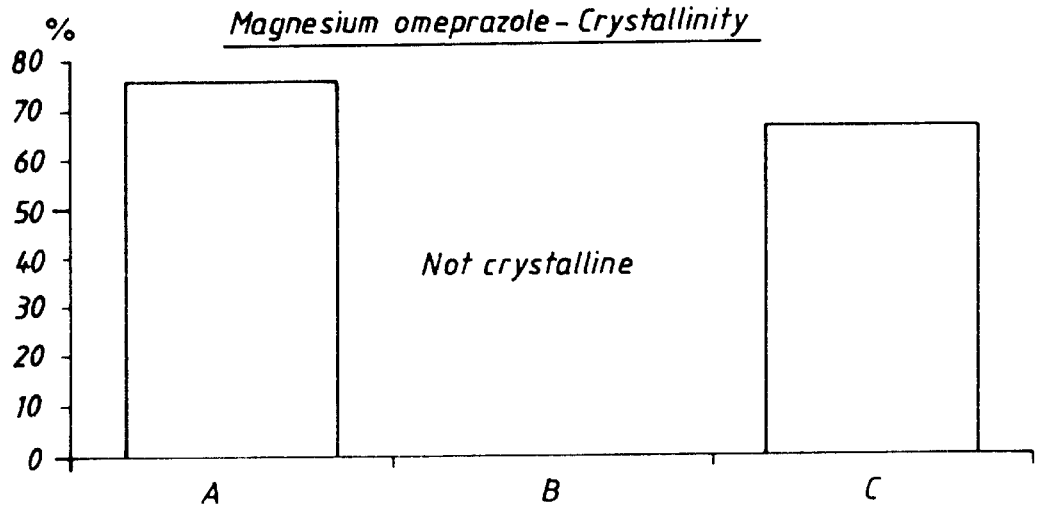

OMEPRAZOLE MAGNESIUM SALT FORM

This is a 371 of PCT/SE94/00680 filed Jul. 8, 1994, now WO 95/01977.

FIELD OF THE INVENTION

The present invention relates to a novel process for manufacturing the magnesium salt of omeprazole; the magnesium salt of omeprazole in a novel physical form, especially the magnesium salt as a product of the novel process; the use of the novel form of the magnesium salt of omeprazole in the manufacture of pharmaceutical formulations; and to the use of the novel form of the magnesium salt of omeprazole in medicine.

BACKGROUND OF THE INVENTION

The compound known under the generic name omeprazole is described i.a. in European patent specification 0005129.

Omeprazole is useful for inhibiting gastric acid secretion and has gastric mucosa protective activity in mammals and man. In a more general sense, omeprazole may be used for prevention and treatment of gastric acid related disorders and gastrointestinal inflammatory diseases in mammal and man, including e.g. gastritis, gastric ulcer and duodenal ulcer.

The term "omeprazole" as used in this specification designates the neutral form of the compound, that is the form without a salt forming cation present.

Certain salts of omeprazole are described in European patent specification 0124495. In said patent specification the requirements and importance regarding storage stability of pharmaceutical preparations are emphasized. Salts possessing superior properties with regard i.a. to storage stability are described in the said European patent specification. In EP 0124495; examples 5 and 6 disclose the synthesis of a magnesium salt of omeprazole.

The isolation and purification in full manufacturing scale of the described magnesium omeprazole salts presents one major problem in that magnesium omeprazole salt crystals are very fragile making processes utilising such crystals less attractive in full scale production. Performing the process without crystallization of the magnesium omeprazole gives a product which is less suitable as a pharmaceutical substance.

In order to use the magnesium salt of omeprazole, in this specification denoted magnesium omeprazole, in full manufacturing scale in preparing pharmaceutical formulations primarily for oral administration, such as tablets, it is necessary that said magnesium omeprazole possesses a combination of properties which makes such full scale manufacturing feasible. One object of the present invention is to provide a process for full scale production of magnesium omeprazole. A further object of the present invention is to provide a novel form of the magnesium salt of omeprazole which can be used in full scale manufacturing of pharmaceutical formulations, such as tablets.

The combination of physical properties of the novel magnesium omeprazole product of the present invention with respect to the degree of crystallinity, particle diameter, density, hygroscopicity, water content and content of other solvents are favorable and permit the manufacture of magnesium omeprazole in a form which possesses the desired properties.

The novel form of magnesium omeprazole can also be formulated into other forms for oral administration and other types of administration such as rectal administration. Examples of formulations are tablets, pellets, granules, capsules, suspensions and suppositories.

The invention

We now provide a novel form of the magnesium salt of omeprazole exhibiting the desired combination of physical properties. This makes full scale production of magnesium omeprazole as well as full scale production of pharmaceutical formulations thereof feasible.

The novel process for the manufacture of magnesium omeprazole also circumvents the above described manufacturing problems and renders possible the recovery and work-up of the magnesium omeprazole substance in traditional chemical process equipment.

It has been found that the following property is significant to obtain such product:

a) Crystalline form, with a degree of crystallinity of not less than 70%, preferably higher than 75% as determined by X-ray powder diffraction It is desirable that the product also exhibits the following properties;

b) Particle size measured as mean mass diameter (MMD) less than 30 $\mu$m, preferably less than 20 $\mu$m as determined by laser diffraction technique.

c) Density between 1.33 g/cm$^3$ and 1.35 g/cm$^3$ as determined by powder pycnometer.

d) Hygroscopicity not exceeding 2% increase of weight upon storage for one month up to 94% relative atmospheric humidity as determined gravimetrically.

e) A content of water of between 5% and 10% by weight as determined by titration according to Karl Fischer.

f) A content of methanol less than 0.1% preferably less than 0.05% by weight as determined by gas chromatography, in case methanol is used as solvent.

In a further aspect, the invention also relates to a process for manufacturing the novel form of magnesium omeprazole. This process is described in more detail below.

The invention relates to all of the aspects given under Field of the invention.

The process for producing the novel form of magnesium omeprazole is characterized by the following consecutive steps a) treating omeprazole or a salt thereof with magnesium alcoholate in a solution b) separating inorganic salts from the reaction mixture c) crystallizing magnesium omeprazole d) isolating the obtained crystalline magnesium omeprazole and, optionally, e) purifying and drying the crystalline magnesium omeprazole using conventional methods.

The process for manufacturing the new product can be described in the following way.

A lower alcohol, such as methanol, ethanol, n-propanol or iso-propanol, preferably methanol, is treated in a solution of polar solvents with a weighed amount of magnesium at temperatures between 0° C. and reflux temperature. The temperature should preferably be between 10 and 30° C. After addition of the magnesium to the solution the temperature can, in a second step be raised further to between 0° C. and reflux temperature, preferably 20–50° C. After termination of the reaction the temperature is reduced to 0–40° C., preferably 10–25° C. Omeprazole or a salt of omeprazole is then added to the solution and after termination of the reaction the mixture is cooled to −10° C. to +20° C., preferably −5° C. to +5° C. The solvent is then evaporated to 40–60% of the initial volume, which makes the inorganic salts precipitate. The precipitate is separated from the reaction solution for example by centrifugation or filtration and the solution is heated to 5° C. to 30° C. whereafter the solution is seeded with magnesium omeprazole crystals. An amount of water, which is approximately equal to the volume of the solution, is added to start the crystallization. The solution is cooled to −10 to +20° C., preferably 0–10° C. to complete the crystallization. The crystals are then separated from the mother liquid for example by centrifugation or filtration and washed with polar solvents preferably an aqueous lower alcohol such as aqueous methanol. Finally, the produced crystals are dried preferably under reduced pressure and heating.

The process for manufacturing the new form of magnesium omeprazole differs from the earlier known processes in that the product is recovered after a controlled crystallization step in aqueous alcohol, preferably methanol by, first, separating the inorganic salts from the mother liquour. The crystallinity resulting from this step is, unexpectedly, higher and the product possesses a higher degree of purity and is more stable to decomposition from uptake of moisture. The drying step can be performed without caking. The new process is possible to perform in conventional chemical process equipment and gives a product with a higher yield than the processes hitherto known.

The following detailed Example 1 will serve to more fully illustrate the process for manufacturing magnesium omeprazole in full scale according to the present invention. In FIGS. 1 and 2 sample A is manufactured according to this example.

EXAMPLE 1

A reactor was filled with 2026 liters of methanol. The stirrer was started and the temperature was adjusted to 20° C. 3,90 kg of magnesium was added to the vessel and immediately thereafter 1,0 liter of $CH_2Cl_2$. The reactor was heated to 40° C. and kept at this temperature for 60 min. It was then cooled to 15° C. before the addition of 99,9 kg of omeprazole. The reactor was kept at this temperature for 60 min and then cooled to 0° C. The temperature was kept at this level for 30 minutes before 1000 l of methanol were evaporated under vacuum and the inorganic solid salt was separated from the liquid first by centrifugation and then by filtration. The liquid was heated to 10° C. and the liquid was seeded with magnesium omeprazole crystals whereafter the magnesium omeprazole salt was precipitated by addition of 900 l of water. The mixture was then cooled to 5° C. After the crystallization had been completed the magnesium omeprazole crystals were centrifuged off and then washed with a mixture of 50 l of methanol and 150 l of water. The produced magnesium omeprazole was dried under reduced pressure finally producing 92,5 kg of crystalline product corresponding to a yield of 81,4%.

The novel form of the magnesium salt of omeprazole according to Example 1 possesses the following properties:

a) Crystalline form, with a degree of crystallinity of 76%, as determined by X-ray powder diffraction.

b) Particle size measured as mean mass diameter (MMD) of 19 μm as determined by laser diffraction technique.

c) Density of 1.342 $g/cm^3$ as determined by powder pycnometer.

d) Hygroscopicity of 1.62% increase of weight upon storage for one month at 94% relative atmospheric humidity as determined gravimetrically.

e) Content of moisture water of 7.6 by weight as determined by titration according to Karl Fischer.

f) Content of methanol of 0.006% by weight as determined by gas chromatography.

A comparison between two different samples of the novel form of magnesium omeprazole of the present invention obtained from two laboratory scale experiments by prior art methods and magnesium omeprazole goes forth from diagrams 1 and 2. In these diagrams sample A represents the novel form of the present invention as manufactured in full scale process equipment. Sample B represents the product of preparation via synthesis by treatment of omeprazole with $Mg(OCH_3)_2$. Sample C represents the product of preparation via treatment of sodium omeprazole with $MgCl_2$.

FIG. 1 shows in diagram 1 that the particle size measured as mean mass diameter of the product of method A is 19 μm which is smaller than the corresponding particle size for the products of method B which is 25 μm and of method C which is greater than 600 μm.

FIG. 2 shows in diagram 2 that the degree of crystallinity of the particles of the product of method A is 76% which is higher than the corresponding figure for the product of sample B, which is 0% and also higher than the corresponding figure of sample C, which 67%.

What is claimed is:

1. An omeprazole magnesium salt having a degree of crystallinity which is higher than 70% as determined by x-ray powder diffraction.

2. The omeprazole magnesium salt according to claim 1 wherein the degree of crystallinity is higher than 75%.

3. The omeprazole magnesium salt according to claim 1 wherein the mean particle diameter as determined by laser diffraction technique is less than 30 μm, and preferably less than 20 μm.

4. The omeprazole magnesium salt according to claim 1 wherein the density is between 1.33 $g/cm^3$ and 1.35 $g/cm^3$ as determined by powder pycnometer.

5. The omeprazole magnesium salt according to claim 1 wherein the water content is between 5% and 10% by weight as determined by titration according to Karl Fischer.

6. The omeprazole magnesium salt according to claim 1 having a solvent content less than 0.1% by weight of solvent as determined by gas chromatography.

7. The omeprazole magnesium salt according to claim 1 having a solvent content less than 0.05% by weight of solvent as determined by gas chromatography.

8. The omeprazole magnesium salt of claim 6 or 7, wherein the solvent is an aqueous alcohol.

9. The omeprazole magnesium salt of claim 6 or 7, wherein the solvent is methanol.

10. The omeprazole magnesium salt according to claim 1 wherein the hygroscopicity is less than 2% increase of weight upon storage for one month at up to 94% relative atmospheric humidity as determined by gravimetry.

11. A process for the manufacture of magnesium omeprazole according to claim 1 comprising in consecutive steps a) treating omeprazole or salt thereof with magnesium alcoholate in a solution, b) separating inorganic salts from the reaction mixture, c) crystallizing magnesium omeprazole by the addition of water, and d) isolating the obtained crystalline magnesium omeprazole.

12. A process according to claim 11 wherein the magnesium alcoholate is magnesium methyl alcoholate.

13. A process according to claim 11 wherein the solvent is methanol.

14. A process according to claim 11 wherein the isolation of the magnesium omeprazole is performed by centrifugal separation of the crystals.

15. A process according to claim 11 wherein the isolation of the magnesium omeprazole is performed by crystallization followed by filtration of the crystals.

16. The process according to claim 11, further comprising the steps of purifying and drying the crystalline magnesium omeprazole.

17. A process according to claim 16 wherein the purification of the magnesium omeprazole crystals is performed by washing the crystals with a solution of polar solvents.

18. A process according to claim 16 wherein the magnesium omeprazole crystals are dried under reduced pressure.

19. A process according to claim 16 wherein the drying of the magnesium omeprazole crystals is performed by evaporating the remaining solvent by heating.

20. In a process for the manufacture of a crystalline magnesium salt comprising, (a) treating omeprazole or a salt thereof with magnesium alcoholate in a solution, (b) crystallizing magnesium omeprazole and (c) isolating the obtained crystalline magnesium omeprazole, wherein the improved process comprises separating inorganic salts from the reaction mixture prior to the crystallization step by the addition of water.

21. A method for inhibiting gastric acid secretion in mammals and man comprising administering to a host in need thereof a therapeutically effective dose of magnesium omeprazole according to any of claims 1 to 4, 6–8 and 10.

22. A method for the treatment of gastric acid related diseases in mammals and man comprising administering to a host in need thereof a therapeutically effective dose of magnesium omeprazole according to any of claims 1 to 4, 6–8 and 10.

* * * * *

UNITED STATES PATENT AND TRADEMARK OFFICE
CERTIFICATE OF CORRECTION

PATENT NO. : 5,900,424

DATED : May 4, 1999

INVENTOR(S) : Kallstrom et al.

It is certified that error appears in the above-identified patent and that said Letters Patent is hereby corrected as shown below:

In claim 21, col. 6, line 9, delete "claims 1 to 4, 6-8" and insert therefor -- claims 1-7 --.

In claim 22, col. 6, lines 13-14, delete "claims 1 to 4, 6-8" and insert therefor -- claims 1-7 --.

Signed and Sealed this

Twenty-eighth Day of September, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,900,424
DATED : May 4, 1999
INVENTOR(S) : Kallstrom et al.

It is certified that error appears in the above-identified patent and that said Letters Patent is hereby corrected as shown below:

On the title page:-

After "[56] References Cited," insert

```
            -- U.S. PATENT DOCUMENTS
    4,738,974    4/1988      514/338
    5,690,960    11/1997     424/480
    5,714,504    3/1998      514/338--
```

Signed and Sealed this

Fourth Day of January, 2000

Attest:

*Attesting Officer*   *Acting Commissioner of Patents and Trademarks*